United States Patent
Crean et al.

(10) Patent No.: US 6,586,419 B1
(45) Date of Patent: *Jul. 1, 2003

(54) PHOTOTHERAPEUTIC INACTIVATION OF OCULAR VIRUSES

(75) Inventors: David H. Crean, Santa Barbara, CA (US); Baruch D. Kupperman, Laguna Beach, CA (US)

(73) Assignees: PDT Systems, Inc., Santa Barbara, CA (US); The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 11 days.

(21) Appl. No.: 08/843,600

(22) Filed: Apr. 16, 1997

(51) Int. Cl.[7] .............................................. A61K 31/555
(52) U.S. Cl. ........................ 514/185; 514/368; 514/680; 514/724; 514/912
(58) Field of Search ................................ 514/365, 680, 514/724, 185, 912

(56) References Cited

PUBLICATIONS

Medline Abstract 75181398 (1975). O'Day et al.*
Medline Abstract 75183024 (1975). Lahav et al.*

* cited by examiner

Primary Examiner—Zohreh Fay
(74) Attorney, Agent, or Firm—Bryan Cave LLP

(57) ABSTRACT

A method for inactivating ocular viral pathogens and for treating associated lesions on tissue by means of selectively activating a tissue-associated photosensitizing agent with light. The photosensitizing agent, preferably tin ethyl etiopurpurin, is administered to a patient to concentrate within the lesionous target tissue of the eye. The photosensitizer-laden target tissue is irradiated with photoactivating light. In pre-clinical in vitro studies, the photoactivated photosensitizer drug within the lesionous target tissue inactivates both cell free Herpes simplex virus (HSV) and cell-associated HSV and cytomegalovirus (CMV). The use of PDT for treating ocular viral diseases reduces the toxicity to the biological system when compared with prior art therapeutic procedures.

22 Claims, 2 Drawing Sheets

CROSS-SECTIONAL VIEW

FUNDUS VIEW

CROSS-SECTIONAL VIEW

FUNDUS VIEW

PHOTOTHERAPEUTIC INACTIVATION OF OCULAR VIRUSES

BACKGROUND OF THE INVENTION

1. Field of the Invention

This invention describes a method for treating ocular viral diseases using photodynamic therapy.

2. Prior Art

In order to give a clinical perspective to the significance of viral ocular infections, for example, cytomegalovirus (CMV) retinitis is the most common ocular apportunistic infection and the leading cause of blindness in patients having Acquired Inmune Deficiency Syndrome (AIDS) 30,000 new case being each year in the United States alone. CMV related retinitis has been fond in 30% of AIDS patents, typically late in their diseases processes. The drugs, ganciclovir, and foscarnet, are effective in the treatment of CMV retinitis. With 82%–100% of patents exhibit an initial response to therapy with either drug. All three drugs are virostatic and require daily systemic intravenous administration for the remainder of the patients lives. Such systemic intravenous administration requires the use of an indevelling catheter which has been associated with high rates of infection. In addition all three drugs exhibit various systemic toxicity; with ganciclovir suppressing the bone marrow and both anywhere and foscarnet causing renal toxicity. The use of these compounds for untying ocular retinitisis discussed by Kupparmann, et al. in *Ann I Opthalmol*, 1993; 115:575–582; and by Holland et al. in *Ophthalmol* 1987; 94:815–823, and by Caleri et al in *Ann. Intern. Med.* 1977 126;257–263, A further discussion of the use of theses drugs for treating a retinitis of viral etiology is presented by various AIDS research groups in the *New England journal of medicine*, 1992; 326; 213–220.

Prior to the advent of antiviral therapy (both anti-CMV and anti-HIV) AIDS patients wit CMV retinitis typically survived only 6 weeks after developing the latter infection. In the current setting of anti-HIV therapy and anti-CMV therapy, median survival has recently been shown to be 8.5 months for patients receiving ganciclovir and 12.6 months for patients receiving foscarnet and more recent studies suggest that median survival is now approaching two years. Longer survival has been associated with greater difficulty related to the continuous suppression of the retinitis over this extended period. Recurrence of the retinitis while on therapy has been reported to occur in 50% of patients within 3 months. (Gross, et al. *Ophthalmol.* 1990; 97:681–686.) Because of the high incidence of reactivation following the initial favorable response to therapy, the current measure of anti-CMV drug efficacy is based on the length of time to recurrence in addition to the initial therapeutic response to the drug. The fact that the efficacy of anti-CMV agents is, in part, measured by the agents' ability to prolong the interval for viral reactivation rather than by its ability to effect permanent suppression of viral activity emphasizes the marginal clinical effectiveness of current regimens wherein ganciclovir, acyclovir and foscarnet are administered intravenously. While these three drugs are preventing blindness in most AIDS patients, many patients are still losing their sight. A therapeutic procedure for controlling viral retinitis which reduces systemic toxicity over the current therapies is needed.

SUMMARY OF THE INVENTION

The present invention discloses a method for treating ocular viral infections comprising the steps of delivering a phototherapeutic agent to a patient, either systemically or locally, so that the agent accumulates within the infected tissue, followed by light irradiation of the photosensitizer-laden infected tissue. A particular phototherapeutic agent, tin ethyl etiopurpurin (SnET2), shows promise for treating viral ophthalmic diseases. Initial results from preclinical testing with SnET2 and light has demonstrated complete inactivation of cell-free Herpes simplex virus (HSV) and cell associated HSV and CMV in vitro.

It is an object of this invention to provide a method for treating viral associated ocular diseases by means of photodynamic therapy.

It is another object of this invention to provide a treatment for viral associated ocular diseases which has a low toxicity to the patient.

It is still another object of this invention to provide a photosensitizer drug which can be administered to selectively localize and accumulate within infected tissue of the eye and which drug, upon illumination with photoactivating light, provides a therapeutic effect.

The features of the invention believed to be novel are set forth with particularity in the appended claims. However, the invention itself, both as to organization and method of operation, together with further objects and advantages thereof may best be understood by reference to the following description taken in conjunction with the accompanying drawings in which:

BRIEF DESCRIPTION OF THE DRAWINGS

FIG. 3b is a fundus view of FIG. 3a.

DESCRIPTION OF THE PREFERRED EMBODIMENTS

Figure 1:
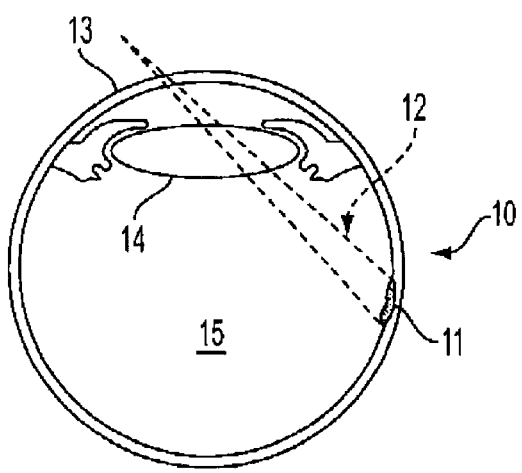
FIG. 1 is a cross-sectional view of an eye containing a viral lesion undergoing phototherapy via transcorneal illumination of a lesion.

Methods for delivering phototherapeutic light having an appropriate wavelength to photoactivate a photosensitizer molecule concentrated within a viral lesion is shown by reference to FIGS. 1 through 6. FIG. 1 is a top cross-sectional view showing an eye 10 having a lesion 11 on the inner (retinal) surface thereof wherein the lesion is of viral origin. Light 12 from a light source (not shown) enters the eye through the cornea 13, passes through the lens 14 and the vitreous humor 15 to interact with and photoactivate the photosensitizer compound concentrated within the lesion 11. Various modes of illumination may be employed to photoactivate the photosensitizer thereby deactivating the viral particles associated with the lesion.

Figure 2:
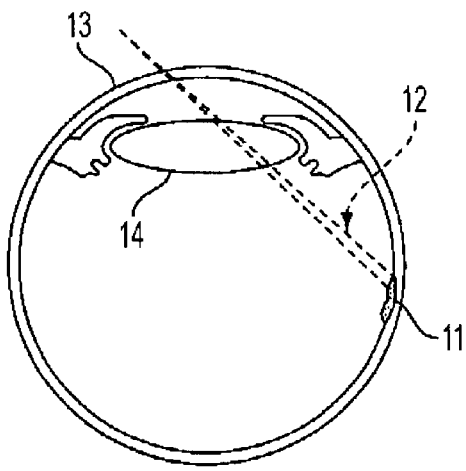
FIG. 2 shows in cross-sectional view an eye wherein a viral lesion is being illuminated with light wherein the area of the field of illumination on the tissue is smaller than the lesion.
Figure 3A:
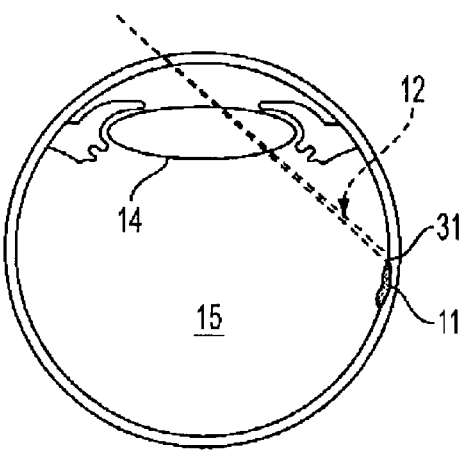
FIG. 3a is a cross-sectional of an eye bearing a viral lesion wherein small areas of retinal tissue on or near the lesion are exposed to light.
Figure 3B:
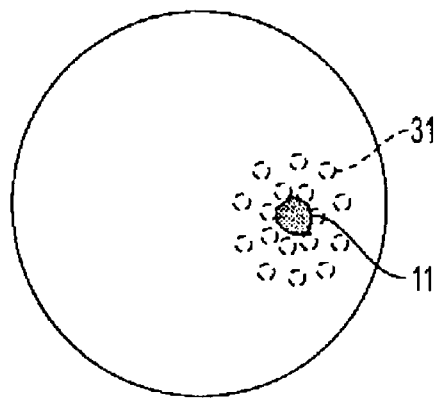
Figure 4A:
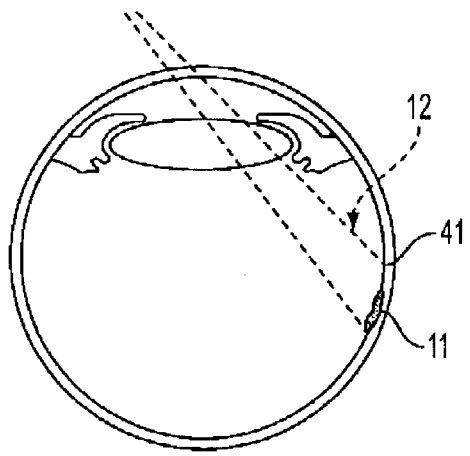
FIG. 4a is a cross-sectional view of an eye bearing a viral lesion wherein transcorneal focal illumination of the viral lesion is accomplished by using a ring of light to encircle the viral lesion.
Figure 4B:
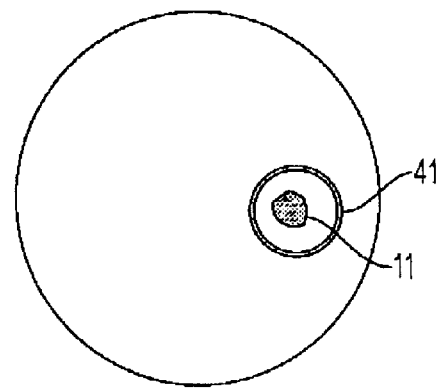
FIG. 4b is a fundus view of the eye as in FIG. 4a above.

Transcorneal focal illumination of viral lesions using an area of light which is slightly larger than the involved lesions is shown in FIG. 1. Transcorneal focal illumination of viral lesions using a patchwork of small illuminated areas which cumulatively cover the areas of the involved lesions is depicted in FIG. 2. Trans-corneal focal illumination of viral lesions using small areas of light exposures to form a pattern of illumination on and around the viral lesions is shown in cross-sectional schematic view in FIG. 3*a*, and in the fundus view in FIG. 3*b*. In FIG. 3*a*, light 12 from an exogenous light source (not shown) impinges upon a region of the retina 31 after passing through the lens 14 and the vitreous 15. The area 31 covered by the light 12 upon the retinal surface is shown in FIG. 3*b*. The sum of the regions 31 comprise a region of the retina including the lesion 11. FIG. 4*a* shows an eye 10 with photoactivating beam of light 12 incident on the retina adjacent to a lesion 11. The beam of light is focused through appropriate optical means to form an illuminated ring around the lesion 11, which ring encircles the lesion 11 as shown in FIG. 4*b*.

Figure 5:
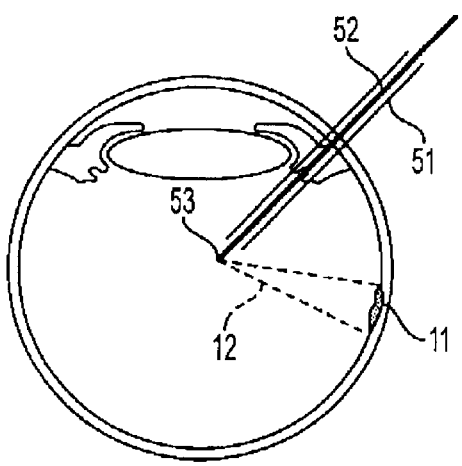
FIG. 5 is a cross-sectional view of an eye bearing a viral lesion wherein the method of illumination is invasive and shows a fiber optic light deliver device inserted intravitreously to illuminate the lesion.
Figure 6:
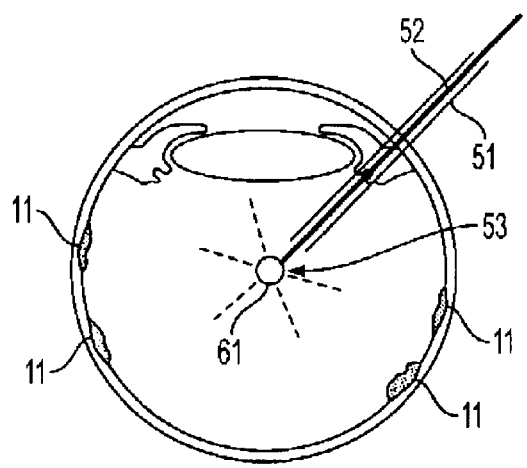
FIG. 6 is a cross sectional view of an eye having a viral lesion thereon wherein illumination of the lesion is accomplished using multi-focal ocular illumination employing intravitreal insertion of an isotropic light source.

Illumination of the target tissue-associated lesion can be accomplished by external light source means as shown in FIGS. 1 through 4, or light can be most preferably delivered by means of a fiber optic light delivery system as shown in FIGS. 5 and 6. In FIG. 5, a fiber optic probe 51 having a fiber optic 52 therewithin, is introduced into the vitreous portion of the eye. The distal end 53 of the optical fiber 52 has focusing means thereon adapted to illuminate the lesion with light 12. Alternatively, a fiber optic probe 51 may have a fiber optic 52 therewithin with a distal end 53 comprising a spherical diffuser tip 61. Light from an external light source is conducted to the spherical diffuser tip 53 by means of the fiber optic 52 within the probe 51. Upon entering the spherical diffuser tip 61, the light is diffusely emitted in a pattern depending upon the particular construction of the diffuser tip 61. Some of the light will encounter photoactivated molecules within the lesions 11 and, upon photoactivation, the photosensitizer molecules therewithin will destroy the virus.

The infectivity of cell-free HSV exposed to SnET2 doses ranging from 10 μg/mL to 0.1 μg/mL and 660 nm light doses of 1.56 J/cm$^2$ are shown in Table 1. Complete inactivation of the virus, >5 log10, was demonstrated with a drug dose of 10 μg/mL and 1 μg/mL and a light dose of 1.56 J/cm$^2$. A partial response, 3 log10, was demonstrated with a drug dose of 0.1 μg/mL and the same light dose. No dark toxicity was observed. The vehicle alone had a slight inhibitory effect on viral infectivity.

TABLE 1

Inactivation of Cell-Free HSV
Drug Dose Response

| | | DARK | | | 660 nm LIGHT (26 mW/cm$^2$, 1.56 J/cm$^2$) | | | | |
|---|---|---|---|---|---|---|---|---|---|
| Saline | Vehicle | 10 μg/mL | 1 μg/mL | 0.1 μg/mL | Saline | Vehicle | 10 μg/mL | 1 μg/mL | 0.1 μg/mL |
| 10$^6$ | 10$^5$ | 10$^6$ | 10$^6$ | 10$^6$ | 10$^6$ | 10$^5$ | <10$^1$ | <10$^1$ | 10$^3$ |

The infectivity of cell-free HSV exposed to 0.1 μg/mL SnET2 and light doses ranging from 1.56 J/cm$^2$ to 25 J/cm$^2$ are shown below in FIG. 2.

TABLE 2

Inactivation of Cell-Free HSV
Light Dose Response

| | Saline | 0.1 μg/mL | 0.1 μg/mL (Light - 26 mW/cm$^2$) | | | | |
|---|---|---|---|---|---|---|---|
| | | DARK | 1.56 J/cm$^2$ | 3.12 J/cm$^2$ | 6.24 J/cm$^2$ | 12.5 J/cm$^2$ | 25 J/cm$^2$ |
| | 106 | 10$^6$ | 10$^3$ | <10$^3$ | <10$^2$ | <10$^1$ | <10$^1$ |

Table 3 summarizes infectivity results with cell-associated HSV exposed to 1 μg/mL and 5 μg/mL SnET2 and a light dose of 15.6 J/cm$^2$. Our results indicated that when a virus is in the presence of cells, inactivation requires higher drug and light doses.

TABLE 3

Inactivation of Cell-Associated HSV

| DARK | LIGHT (52 Mw/cm$^2$, 1.56 J/cm$^2$) | |
|---|---|---|
| Saline | 1 μg/mL | 5 μg/mL |
| 10$^7$ | 10$^3$ | <10$^3$ |

Table 4 summarizes initial work with the cell associated CMV. Infectivity results indicated that complete inactivation, 2–5 log10, can be achieved at drug and light doses of 1–10 μg/mL and 15.6 J/cm$^2$ respectively.

TABLE 4

Inactivation of Cell-Associated CMV

| DARK | | LIGHT (52 Mw/cm$^2$, 1.56 J/cm$^2$) | | |
|---|---|---|---|---|
| Saline | 10 μg/mL | 1 μg/mL | 5 μg/mL | |
| <10$^5$ | n.d. | >10$^3$ | >10$^3$ | CMV 1:2 |
| 10$^6$, 10$^5$ | <10$^5$, n.d. | <10$^2$, 10$^4$ | <10$^2$, 10$^3$ | CMV 1:10 |

To inactivate virus from a frozen viral stock with SnET2 and light doses, the following procedure was employed. Following light treatment, undiluted virus and drug/virus mixture were diluted 10-fold up to 1:10$^6$. All dilutions were used to infect sub-confluent, heat-shocked cultures of a cell line plated in tissue cultures of 24 well plate in triplicates. The infected cultures were treated with antibody against the major viral capside protein. An alkaline phosphatase labeled antibody to mouse IgG was then added followed by the alkaline phosphatase substrate. This produced a colored reaction which can be monitored microscopically in positive wells. The infected cells were characterized by a dark purple coloration in the nucleus. Viral titer or viral infectivity was determined by the last viral concentration that gave at least one infected cell per well.

In the present method for treating viral ocular pathogens various photosensitive agents may be employed. Photosensitizing agents which are deemed to be suitable candidates for further consideration are set forth below in Table 5. A characteristic of many of these compounds is the presence of a fused tetrapyrrolic core structure. These agents may be preferentially taken up by and accumulated within viral-containing tissues. Following bioconcentration of photosensitizer in the diseased ocular tissue, the viruses and/or tissues are exposed to a light of a specific wavelength for an appropriate time interval and dose resulting in selective viral kill and tissue destruction while minimizing healthy, normal tissue damage. This approach has been termed phototherapy or photodynamic therapy (PDT) depending upon the type of mechanism involved.

TABLE 5

Pharmacologically-Active Photosensitizing Compound/Classes

1. Pyrrole-derived macrocyclic compounds
2. Naturally-occurring or synthetic porphyrins and derivatives thereof
3. Naturally-occurring or synthetic chlorins and derivatives thereof
4. Naturally-occurring or synthetic bacteriachlorins and derivatives thereof
5. Synthetic isobacteriochlorins and derivatives thereof
6. Phthalocyanines and derivatives thereof
7. Napthalocyanines and derivatives thereof
8. Porphycenes and derivatives thereof
9. Sapphyrins and derivatives thereof
10. Texaphyrins and derivatives thereof
11. Anthrapryazoles and derivatives thereof
12. Phenoxaxine and derivatives thereof
13. Phenothiazine and derivatives thereof
14. Chaloorganapyrylium dye and derivatives thereof
15. Triairylmethanes and derivatives thereof
16. 5-Aminolevulinic acid
17. Inhibitors of protoporphyrin oxidase
18. Psoralens and derivatives thereof.

While particular embodiments of the present invention have been illustrated and described, it would obvious to those skilled in the art that various other changes and modifications can be made without departing from spirit and scope of the invention. The use of the method for treating ocular lesions on the retina has been presented as an exemplary use of the method for teaching purposes. It is, for example, clear that corneal lesions as well as retinal lesions may be treated by the method disclosed herein. Similarly, transcorneal focusing of treatment light by using the optical properties of the lens of the eye is exemplary. Other optical lens systems may be employed to direct treatment light to a viral infected tissue. It is therefore intended to cover in the appended claims all such changes and modifications that are within the scope of the invention.

What we claim is:

1. A method for treating eye tissue having a viral lesion below the surface of the cornea, comprising the steps of:
    (a) delivering a photosensitive compound to the tissue such that a therapeutic dose of the photosensitive compound is concentrated within the tissue; and
    (b) illuminating the tissue by transcorneal focal illumination such that light is delivered through the cornea and focused on targeted tissue below the surface of the cornea.

2. The method of claim 1 wherein the lesion is illuminated using an area of light exposure that is slightly larger than the lesion.

3. The method of claim 1 wherein the lesion is illuminated using a plurality of areas of light exposure that cumulatively cover the area of the lesion.

4. The method of claim 1 wherein tissue surrounding the lesion is illuminated using a plurality of areas of light exposure to form one or more of concentric rings around the lesion.

5. The method of claim 1 wherein tissue surrounding the lesion is illuminated using a ring of light around the lesion.

6. The method of claim 1 wherein the lesion is a retinal lesion.

7. The method of claim 1 wherein the tissue is illuminated with a therapeutically effective dose of light of approximately 0.5–100 J/cm$^2$.

8. The method of claim 1 wherein the tissue is illuminated with a therapeutically effective dose of light of approximately 1.56–25 J/cm$^2$.

9. The method of claim 1 wherein the photosensitive compound is selected from the group consisting of:
    a. Pyrrole-derived macrocyclic compounds;
    b. Naturally-occurring or synthetic porphyrins and derivatives thereof;
    c. Naturally-occurring or synthetic chlorins and derivatives thereof;
    d. Naturally-occurring or synthetic bacteriochlorins and derivatives thereof;
    e. Synthetic isobacteriochlorins and derivatives thereof;
    f. Phthalocyanines and derivatives thereof;
    g. Naphthalocyanines and derivatives thereof;
    h. Porphycenes and derivatives thereof;
    i. Sapphyrins and derivatives thereof;
    j. Texaphyrins and derivatives thereof;
    k. Anthrapryzsoles and derivatives thereof;
    l. Phenoxazine and derivatives thereof;
    m. Phenothiazine and derivatives thereof;
    n. Chaloorganapyrylium dye and derivatives thereof;
    o. Triarylmethanes and derivatives thereof;
    p. 5-Aminolevulinic acid;
    q. Inhibitors of protorphyrin oxidase; and
    r. Psoralens and derivatives thereof.

10. The method of claim 1 wherein the photosensitive compound comprises a fused tetrapyrrolic core.

11. A method for treating eye tissue having a viral lesion below the surface of the cornea, comprising the steps of:
(a) delivering a photosensitive compound to the tissue such that a therapeutic dose of the photosensitive compound is concentrated within the tissue; and
(b) illuminating the tissue by intravitreal fiberoptic delivery of light such that a light source is inserted into the vitreous to deliver light to targeted tissue below the surface of the cornea.

12. The method of claim 11 wherein the lesion is illuminated using an area of light exposure that is slightly larger than the lesion.

13. The method of claim 11 wherein the lesion is illuminated using a plurality of areas of light exposure that cumulatively cover the area of the lesion.

14. The method of claim 11 wherein tissue surrounding the lesion is illuminated using a plurality of areas of light exposure to form one or more concentric rings of light around the lesion.

15. The method of claim 11 wherein tissue surrounding the lesion is illuminated using a ring of light around the lesion.

16. The method of claim 11 wherein the tissue is illuminated by intravitreal insertion of a substantially isotropic light source.

17. The method of claim 11 wherein the tissue is illuminated by intravitreal insertion of a fiber optic comprising a substantially spherical diffuser tip.

18. The method of claim 11 wherein the lesion is a retinal lesion.

19. The method of claim 11 wherein the tissue is illuminated with a therapeutically effective dose of light of approximately 0.5–100 J/cm$^2$.

20. The method of claim 11 wherein the tissue is illuminated with a therapeutically effective dose of light of approximately 1.56–25 J/cm$^2$.

21. The method of claim 11 wherein the photosensitive compound is selected from the group consisting of:
a. Pyrrole-derived macrocyclic compounds;
b. Naturally-occurring or synthetic porphyrins and derivatives thereof;
c. Naturally-occurring or synthetic chlorins and derivatives thereof;
d. Naturally-occurring or synthetic bacteriochlorins and derivatives thereof;
e. Synthetic isobacteriochlorins and derivatives thereof;
f. Phthalocyanines and derivatives thereof;
g. Naphthalocyanines and derivatives thereof;
h. Porphycenes and derivatives thereof;
i. Sapphyrins and derivatives thereof;
j. Texaphyrins and derivatives thereof;
k. Anthrapryzsoles and derivatives thereof;
l. Phenoxazine and derivatives thereof,
m. Phenothiazine and derivatives thereof;
n. Chaloorganapyrylium dye and derivatives thereof;
o. Triarylmethanes and derivatives thereof;
p. 5-Aminolevulinic acid;
q. Inhibitors of protorphyrin oxidase; and
r. Psoralens and derivatives thereof.

22. The method of claim 11 wherein the photosensitive compound comprises a fused tetrapyrrolic core.

* * * * *